(12) United States Patent
Minh et al.

(10) Patent No.: US 7,034,528 B2
(45) Date of Patent: Apr. 25, 2006

(54) METHODS FOR FORMATION EVALUATION BASED ON MULTI-DIMENSIONAL REPRESENTATION OF NUCLEAR MAGNETIC RESONANCE DATA

(75) Inventors: Chanh Cao Minh, Katy, TX (US); Nicholas J. Heaton, Houston, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 0 days.

(21) Appl. No.: 10/604,869

(22) Filed: Aug. 22, 2003

(65) Prior Publication Data
US 2004/0169511 A1    Sep. 2, 2004

Related U.S. Application Data

(60) Provisional application No. 60/450,412, filed on Feb. 27, 2003.

(51) Int. Cl.
*G01V 3/00* (2006.01)

(52) U.S. Cl. ..................................................... 324/303
(58) Field of Classification Search ................ 324/303, 324/306, 307, 309, 310
See application file for complete search history.

(56) References Cited

U.S. PATENT DOCUMENTS

| | | | |
|---|---|---|---|
| 5,696,448 A | 12/1997 | Coates et al. | |
| 6,121,774 A | 9/2000 | Sun et al. | |
| 6,166,543 A | 12/2000 | Sezginer et al. | |
| 6,229,308 B1 | 5/2001 | Freedman | |
| 6,232,778 B1 | 5/2001 | Speier et al. | |
| 6,255,818 B1 | 7/2001 | Heaton et al. | |
| 6,366,087 B1 | 4/2002 | Coates et al. | |
| 6,400,147 B1 | 6/2002 | Toufaily et al. | |
| 6,459,992 B1 | 10/2002 | Freedman et al. | |

(Continued)

FOREIGN PATENT DOCUMENTS

GB    2398876    9/2004

OTHER PUBLICATIONS

Hurlimann, M.D. et al., "The diffusion-spin relaxation time distribution function as an experimental probe to characterize fluid mixtures in porous media," Journal of Chemical Physics, vol. 117. No. 22, Dec. 2002, pp. 10223-10232.

*Primary Examiner*—Diego Gutierrez
*Assistant Examiner*—Dixomara Vargas
(74) *Attorney, Agent, or Firm*—Kevin P. McEnaney; Bryan L. White; Victor H. Segura

(57) ABSTRACT

A method is disclosed for interpretation of multi-dimensional nuclear magnetic resonance data taken on a sample of an earth formation. Specifically, a set of NMR data is acquired for a fluid sample located either in a borehole or in a laboratory environment. From the set of NMR data, a multi-dimensional distribution is calculated using a mathematical inversion that is independent of prior knowledge of fluid sample properties. The multi-dimensional distribution is graphically displayed on a multi-dimensional map. Each fluid instance or artifact visible on the graph is identified as representing a probable existence of a detected fluid. One or more quantitative formation evaluation answers for one or more fluid instances is computed based on the multi-dimensional distribution associated with the respective fluid instance.

3 Claims, 12 Drawing Sheets

U.S. PATENT DOCUMENTS

| | | |
|---|---|---|
| 6,498,484 B1 | 12/2002 | Sun et al. |
| 6,518,757 B1 | 2/2003 | Speier |
| 6,522,137 B1 | 2/2003 | Sun et al. |
| 6,522,138 B1 | 2/2003 | Heaton |
| 6,534,980 B1 | 3/2003 | Toufaily et al. |
| 6,559,638 B1 | 5/2003 | Adelerhof |
| 6,570,382 B1 | 5/2003 | Hurlimann et al. |
| 6,573,716 B1 | 6/2003 | Toufaily et al. |
| 6,765,380 B1 * | 7/2004 | Freedman et al. .......... 324/303 |
| 2002/0105326 A1 | 8/2002 | Hurlimann et al. |

* cited by examiner

METHODS FOR FORMATION EVALUATION BASED ON MULTI-DIMENSIONAL REPRESENTATION OF NUCLEAR MAGNETIC RESONANCE DATA

CROSS REFERENCE TO RELATED APPLICATIONS

This invention claims priority pursuant to 35 U.S.C. §119 of U.S. Provisional Patent Application Ser. No. 60/450,412, filed on Feb. 27, 2003. This Provisional Application is hereby incorporated by reference in its entirety.

BACKGROUND OF INVENTION

Both water and hydrocarbons in earth formations produce detectable NMR signals. It is desirable that the signals from water and hydrocarbons be separable so that hydrocarbon-bearing zones may be identified. However, it is not always easy to distinguish which signals are from water and which are from hydrocarbons. Various methods have been proposed to separately identify water and hydrocarbon signals.

The differential spectrum (DSM) and shifted spectrum (SSM) methods proposed by Akkurt et. al. in "NMR Logging of Natural Gas Reservoirs" Paper N. Transactions of the Society of Professional Well Log Analysts (SPWLA) Annual Logging Symposium, 1995, compare $T_2$ distributions derived from two Carr-Purcell-Meiboom-Gill (CPMG) measurements performed with different polarization times (DSM) or echo-spacings (SSM). A modification to these methods, known as time domain analysis (TDA), was later introduced by Prammer et al. in "Lithology-Independent Gas Detection by Gradient-NMR Logging," SPE paper 30562, 1995. In TDA, "difference" data are computed directly in the time domain by subtracting one set of the measured amplitudes from the other. The difference dataset is then assumed to contain only light oil and/or gas. In TDA, relative contributions from light oil or gas are derived by performing a linear least squares analysis of the difference data using assumed NMR responses for these fluids. Both DSM and TDA assume that the water signal has substantially shorter $T_1$ relaxation times than those of the hydrocarbons. This assumption is not always valid, however. Most notably, this assumption fails in formations where there are large pores or where the hydrocarbon is of intermediate or high viscosity. The SSM method and its successor, the enhanced diffusion method (EDM) proposed by Akkurt et. al. in "Enhanced Diffusion: Expanding the Range of NMR Direct Hydrocarbon Typing Applications", Paper GG. Transactions of the Society of Professional Well Log Analysts (SPWLA) Annual Logging Symposium, 1998, separate gas, oil and water contributions based on changes in the $T_2$ distributions that result from changes in the echo spacing of CPMG measurements. The methods are applicable in a limited range of circumstances and the accuracy of the result is significantly compromised by incomplete separation of water and hydrocarbon signals in the $T_2$ domain. Moreover, these methods are designed to function with CPMG sequences. However, with the diffusion-based methods, CPMG pulse sequences provide poor signal to noise ratios due to the reduced number of echoes that can be measured. A strategy for combining and selecting these different NMR methods has been described recently by Coates et al. in U.S. Pat. No. 6,366,087 B1.

The diffusion-editing (DE) pulse sequence by Hürlimann et al. provides a different approach. See M. D. Hürlimann et al., "*Diffusion-Editing: New NMR Measurement of Saturation and Pore Geometry*," paper presented at the 2002 Annual Meeting of the Society of Professional Well Log Analysts, Osio, Japan, Jun. 2–5; see also, U.S. Pat. No. 6,570,382, filed on Nov. 28, 2000, by Hürlimann. This patent is assigned to the same assignee as the present invention and is hereby incorporated by reference. DE pulse sequences are similar to the CPMG sequences except that the initial two echoes are acquired with longer echo spacings and the third and subsequent echoes are acquired with shorter echo spacings. In DE pulse sequences, diffusion information is encoded during the acquisition of the first two echoes, whereas the third and subsequent echoes provide bulk and surface relaxation time information with relatively little attenuation of the signal by diffusion. Using a conventional CPMG sequence to encode the diffusion information requires a long inter-echo spacing, which results in poor bulk and surface relaxation time information because diffusion decay attenuates the signal after relatively few echoes. Consequently, a suite of data acquired with DE sequences provides better diffusion information and signal-to-noise ratio in the spin-echo data, as compared to an analogous suite acquired with CPMG sequences. Therefore, DE sequences can provide more accurate and robust computations of brine and oil $T_2$ distributions than CPMG sequences.

In addition to DE sequences, specialized interpretation methods have been developed for NMR data in order to further enhance hydrocarbon detection. These methods typically apply forward modeling to suites of NMR data acquired with different parameters. The suite of NMR data are typically acquired with different echo spacings (TE) or polarization times (WT), and sometimes acquired with different magnetic field gradients (G). DE sequences are one example of such data acquisition. Two exemplary methods include: the MACNMR proposed by Slijkerman et al., SPE paper 56768, "Processing of Multi-Acquisition NMR Data", 1999, and the Magnetic Resonance Fluid characterization (MRF) methoddisclosed in U.S. Pat. No. 6,229,308 B1 issued to Freedman and assigned to the assignee of the present invention ("the Freedman patent"). The Freedman patent is hereby incorporated by reference.

The MRF method is capable of obtaining separate oil and water $T_2$ distributions. This method uses a Constituent Viscosity Model (CVM), which relates relaxation time and diffusion rates to constituent viscosities whose geometric mean is identical to the macroscopic fluid viscosity. With the MRF method, estimates for water and hydrocarbon volumes are obtained by applying a forward model to simulate the NMR responses to a suite of NMR measurements acquired with different parameters. Specifically, The MRF technique is based on established physical laws which are calibrated empirically to account for the downhole fluid NMR responses. By using realistic fluid models, MRF aims to minimize the number of adjustable parameters to be compatible with the information content of typical NMR log data. Since the model parameters are by design related to the individual fluid volumes and properties, determination of the parameter values (i.e. data-fitting) leads directly to estimates for petrophysical quantities of interest.

The forward-model approach relies on the validity of the fluid models employed. In "non-ideal" situations where fluid NMR responses deviate from the model behavior (oil-wet rocks, restricted diffusion), these techniques may lead to erroneous answers. In some circumstances, "nonideal"responses may be identified by poor fit-quality, in which case the fluid models can be adjusted by modifying the appropriate model parameter. However, it may not be obvious which element of the fluid model should be modified and what modification is needed.

Another approach developed by Schlumberger, based on a maximum entropy principle (MEP), consists of a general model-independent method to analyze complex fluids data acquired with NMR logging instruments and present the results in a visually attractive and easy-to-understand format, hereby referred to as Diffusion-Relaxation maps, or D-T2 maps. These maps have been used to understand cases where model-based analysis gives unsatisfactory results because of deviations of NMR properties from the "ideal" behavior assumed in the models. These situations can arise due to anomalous fluid/rock interactions such as restricted diffusion, mixed-wettability and internal gradients. Deviations from the default properties have also been observed for certain crude oils, leading to inaccurate predictions in the model analysis. Through the use of D-T2 maps, the MEP approach provides a simple graphical representation of the data that can be used to identify fluid responses in all environments. Diffusion-Relaxation maps are further described in commonly assigned U.S. Pat. Nos. 6,570,382 and 6,462,542.

While these prior art methods are useful in predicting the presence of hydrocarbons in the formations, it is desirable to have simpler methods that can predict the presence of hydrocarbons in the formations from NMR data and are generally applicable to NMR data acquired with different pulse sequences. Furthermore, while two and three dimensional visualization has been developed to obtain primarily qualitative information, it is desirable to have quantitative interpretation techniques that can provide accurate fluid-characterization results.

SUMMARY OF INVENTION

According to one aspect of the disclosed subject matter a method is described for interpretation of multi-dimensional nuclear magnetic resonance data taken on a sample of an earth formation. Specifically, a set of NMR data is acquired for a fluid sample located either in a borehole or in a laboratory environment. From the set of NMR data, a multi-dimensional distribution is calculated using a mathematical inversion that is independent of prior knowledge of fluid sample properties. The multi-dimensional distribution is graphically displayed on a multi-dimensional map. Each fluid instance or artifact visible on the graph is identified as representing a probable existence of a detected fluid. One or more quantitative formation evaluation answers for one or more fluid instances are computed based on the multi-dimensional distribution associated with the respective fluid instance.

According to another aspect, quantitative formation evaluation answers are determined from the multi-dimensional distribution of NMR data by initially determining a set of model parameters which represent aspects of the multi-dimensional distribution. A model dependent inversion is then applied to compute the fluid properties.

According to another aspect, quantitative formation evaluation answers are determined from the multi-dimensional distribution of NMR data through a point-and-click approach. One or more fluid artifacts are selected from a multi-dimensional map of the NMR data using a computer mouse or an automatic edge selection application. The amplitude is integrated over the selected region to determine properties of the fluid associated with the selected region.

According to another aspect, quantitative formation evaluation answers are determined from the multi-dimensional distribution of NMR data by determining a mean diffusion value across a region of a diffusion-T2 relaxation distribution. The mean diffusion is used to determine properties of the fluid associated with the selected region.

DETAILED DESCRIPTION

The disclosed subject matter describes quantitative methods to interpret two-dimensional nuclear magnetic resonance (NMR) maps derived from common NMR formation evaluation measurements. Although other values may be used, a preferred embodiment is primarily discussed herein based on diffusion vs. $T_2$ (D-T2) maps. According to the present invention, D-T2 maps can be used to help in the selection of parameters for application to existing model-based inversion codes. Further, complete petrophysical answers (porosity, permeability, fluids volumes, saturations, oil viscosity etc.) can be derived directly from the D-T2 maps. To take advantage of the visual appeal of the maps, the proposed methods are interactive and, according to an embodiment, consist of sequential point-and-click procedures.

Figures 1, 2:
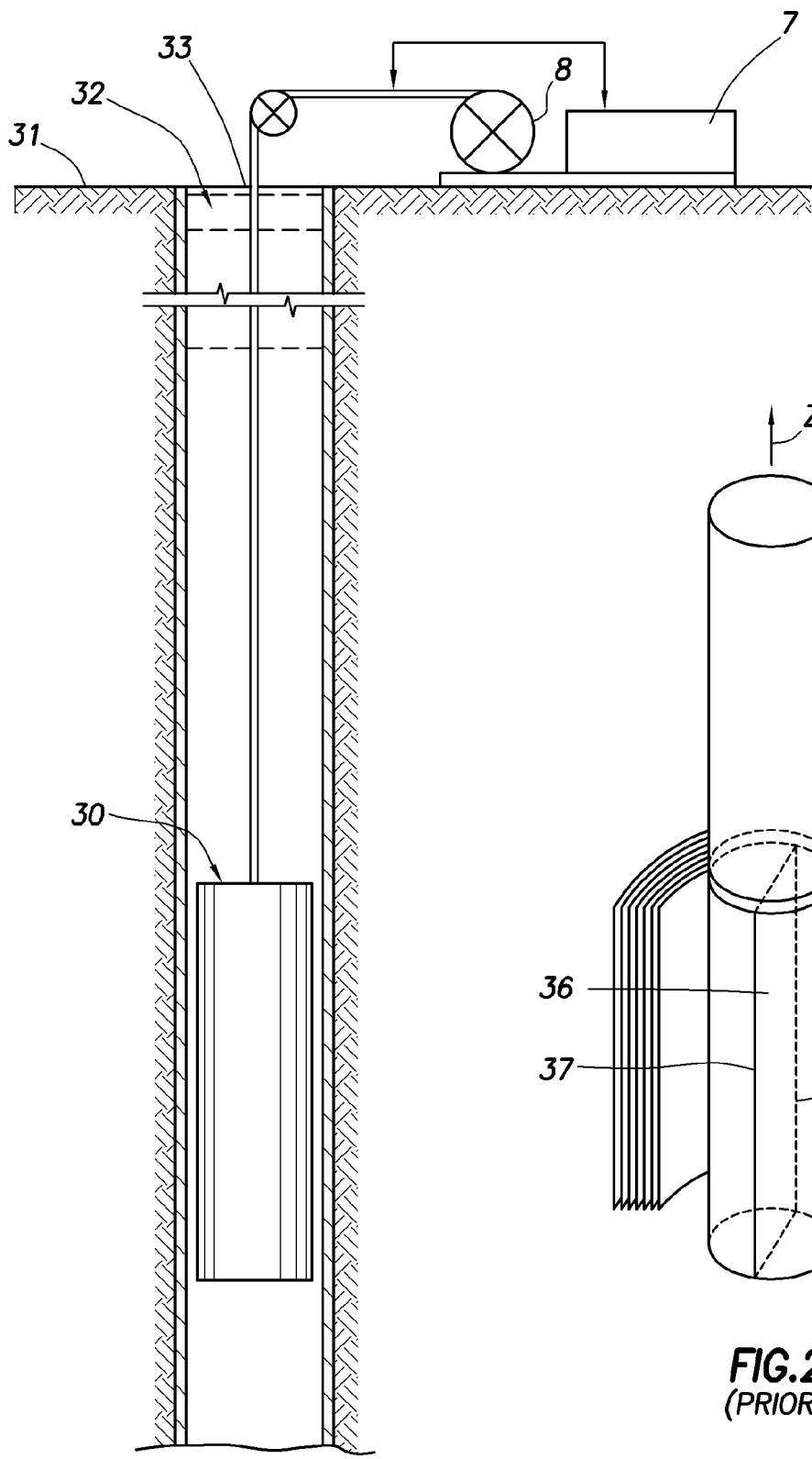
FIG. 1 is a diagram of an exemplary downhole nuclear magnetic resonance data acquisition system.
FIG. 2 is a more detailed diagram of the system of FIG. 1.

Acquisition of NMR measurements according to embodiments of the invention may be accomplished with various methods of NMR measurements known in the art. For example, the measurements may be performed in a laboratory using a sample removed from an earth formation. Alternatively, the NMR measurements may be performed in a logging operation using a wireline tool, a logging-while-drilling or measurement-while-drilling tool, or a formation tester. FIG. 1 illustrates a schematic of an NMR logging system. In FIG. 1, a NMR logging tool 30 for investigating earth formations 31 traversed by a borehole 32 is shown. The NMR logging device 30 is suspended in the borehole 32 on an armored cable 33, the length of which substantially determines the relative axial depth of the device 30. The cable length is controlled by suitable means at the surface such as a drum and winch mechanism 8. Surface equipment 7 can be of conventional type and can include a processor subsystem which communicates with downhole equipment including NMR logging device 30.

Figure 3:
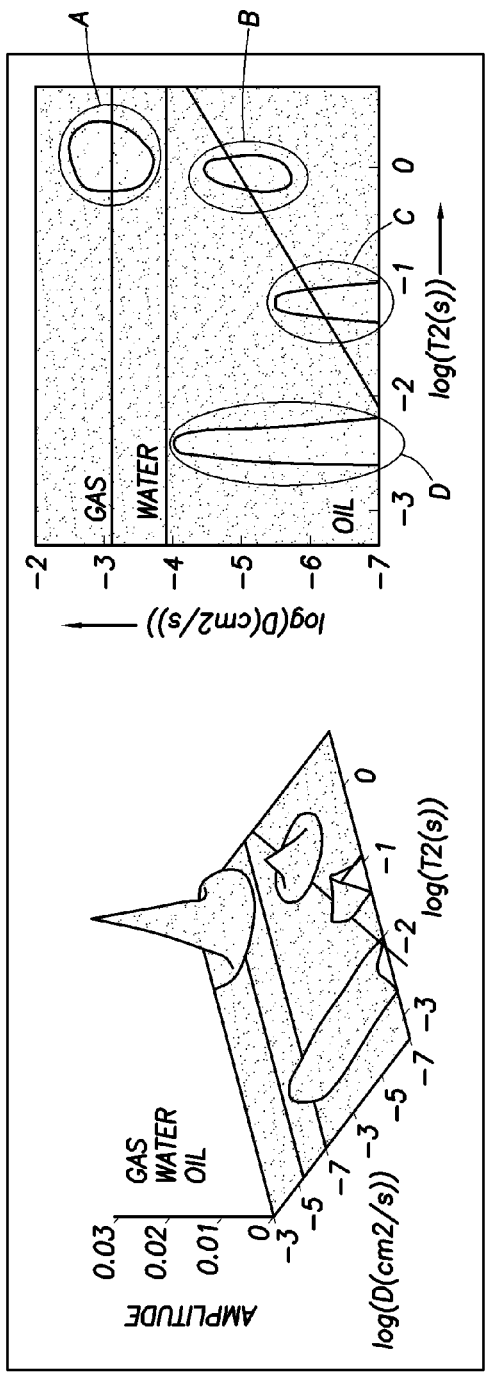
FIG. 3 is a multi-dimensional map or graph for displaying NMR data.

The NMR logging device 30 can be any suitable nuclear magnetic resonance logging device; it may be one for use in wireline logging applications as shown in FIG. 3, or one that can be used in logging-while-drilling (LWD) or measurement-while-drilling (MWD) applications. In addition, the NMR logging device 30 may be part of any formation tester known in the art, such as that sold under the trade name of MDT™ by Schlumberger Technology Corporation (Houston, Tex.). The NMR logging device 30 typically includes a means for producing a static magnetic field in the formations, and a radio frequency (RF) antenna means for producing pulses of magnetic field in the formations and for receiving the spin echoes from the formations. The means for producing a static magnetic field may comprise a permanent magnet or magnet array, and the RF antenna means for producing pulses of magnetic field and receiving spin echoes from the formations may comprise one or more RF antennas.

Figure 4:
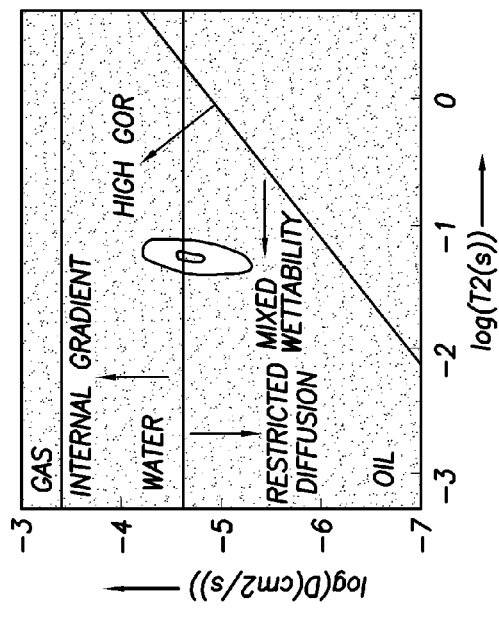
FIG. 4 is a NMR data map showing non-ideal effects on the NMR data.

FIG. 2 illustrates a schematic of some of the components of one type of NMR logging device 30. FIG. 4 shows a first centralized magnet or magnet array 36 and an RF antenna 37, which may be a suitably oriented coil or coils. FIG. 2 also illustrates a general representation of closely-spaced cylindrical thin shells, 38-1, 38-2 . . . 38-N, that can be frequency selected in a multi-frequency logging operation. One such device is disclosed in U.S. Pat. No. 4,710,713. In FIG. 2, another magnet or magnet array 39 is shown. Magnet array 39 may be used to pre-polarize the earth formation ahead of the investigation region as the logging device 30 is raised in the borehole in the direction of arrow Z. Examples of such devices are disclosed in U.S. Pat. Nos. 5,055,788 and 3,597,681.

Turning now to FIG. 3, shown is an exemplary D-T2 map with NMR spin echo data presented as amplitudes versus diffusion (D) and relaxation (T2). The map shown in the left panel is a three-axis perspective view. The right panel provides a more practical representation of D-T2 map as a two-axis map. However, it should be noted that the disclosed methods may be applied a dataset having any number of dimensions, 2-D, 3-D, 4-D, etc. Furthermore, it should be noted that although D-T2 maps are discussed herein for exemplary purposes, the disclosed methods can be equally as effective in obtaining quantitative formation evaluation answers based on many other combinations of NMR data properties (D, T1, T2, T1/T2, etc.).

In the context of the two-axis D-T2 map, the diffusion amplitude is represented according to a color-coding scheme. The differences of diffusion properties among gas, water and various viscosity oils are captured by the D-T2 map and shown as separate and distinct peaks. Specifically, the color grouping at A, also herein referred to as an artifact or a fluid instance, represents the probable detection of a first fluid. Similarly, the lighter color groupings or fluid instances at B, C and D also represent the probable detection of three additional fluids. The theoretical responses of water, oil, and gas are overlaid on the maps to help the interpretation. Thus, for grouping or instance A, it is likely that the fluid is gas because its peak lies near the theoretical gas diffusion value. For groupings B and C, it is likely the fluids are varying viscosities or phases of oil, lying along the theoretical oil diffusion line. Finally, it is likely that grouping or instance D is water subject to restricted diffusion (discussed below).

According to one embodiment, the cross-plot of FIG. 3 is model-independent. This means that no predetermined diffusion values or limits are imposed in the calculation to obtain NMR measurements from the spin echo data. Although others exist, one example of a model-independent calculation is the previously mentioned MEP approach. Returning to FIG. 3, in order to assist interpretation of the NMR data, an overlay of theoretical responses of water, oil and gas is helpful.

As mentioned, previous attempts to determine quantitative formation evaluation answers have been based on the model predetermined values of diffusion and T2 relaxation parameters of the fluids. In addition, it has been required to select a fluid model based upon a best guess as to which fluids will be detected. Needless to say, any inaccuracies in the initial estimates of the fluid model and the fluids parameters create inaccuracies in the final answers. FIG. 4 graphically illustrates some exceptions to common ideal models: 1) Internal gradient pulls data in the up-arrow direction (such that water could be mistaken for gas), 2) Restricted diffusion pulls data in the other direction as indicated by the down arrow (such that water could be mistaken for oil), 3) Mixed wettability pulls the oil data to the left (such that the oil volume/saturation are computed too low), and 4) high GOR (Gas Oil Ratio) cause oils to shift along the North-East trend (such that oils could be mistaken for water or gas).

Figure 5:
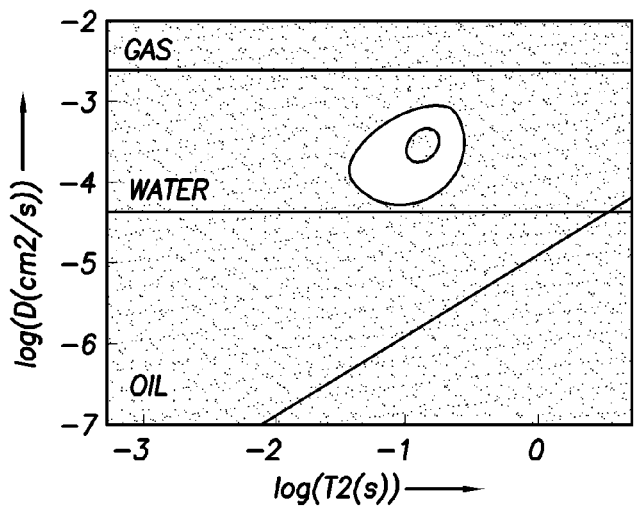
FIG. 5 is another NMR data map showing non-ideal effects on the NMR data.

For example, FIG. 5 illustrates an effect of internal gradient effect on a NMR fluid response. The internal gradient adds to the tool gradient and hence, diffusion is higher than expected. The sample is a clay-rich sandstone in a known water-bearing zone of a well drilled with water-base mud. As such, the calculated diffusion values appear higher than the expected result, indicated by the water diffusion line overlay.

Figure 6:
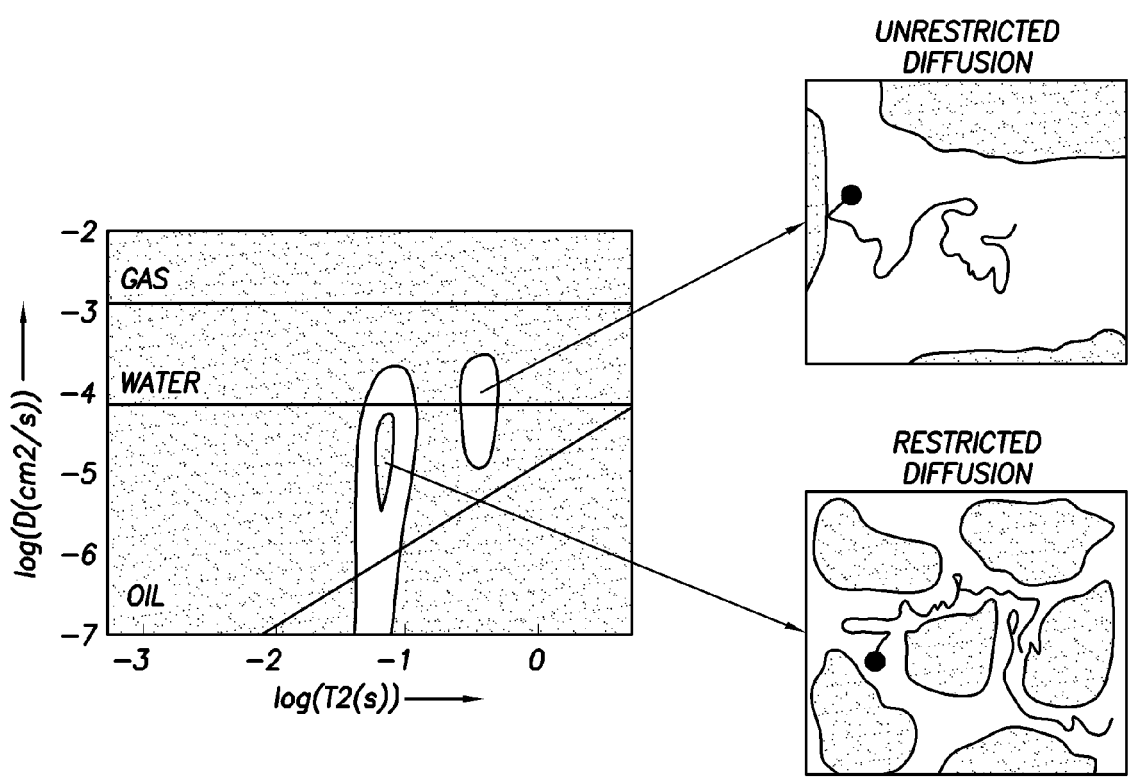
FIG. 6 is another NMR data map showing non-ideal effects on the NMR data.

Another example is shown in FIG. 6, which illustrates an effect of restricted diffusion in a known carbonate dominated formation. The free water undergoes unrestricted diffusion in large pores and agrees with the theoretical response. The bound water is trapped in smaller pores and therefore experiences restricted diffusion. The result is one peak, representing the free water, at the expected water diffusion overlay and a second peak, representing the bound water, stretched across a range of diffusion values, even crossing into values indicative of hydrocarbon presence.

Figure 7:
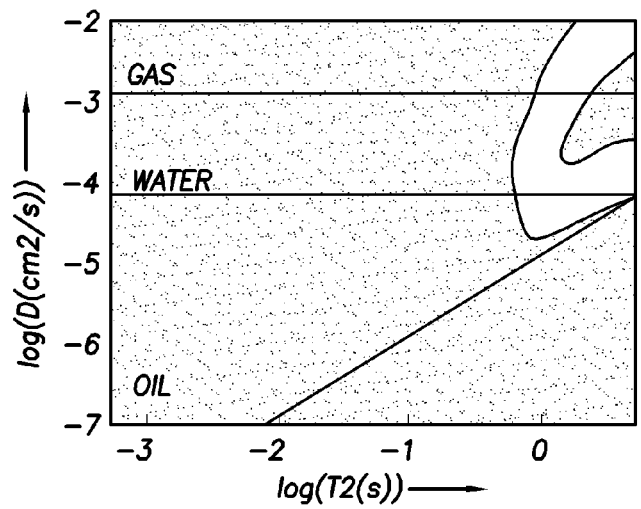
FIG. 7 is another NMR data map showing non-ideal effects on the NMR data.

Yet another example, shown in FIG. 7, illustrates gas in high-permeability sandstone reservoirs in the Middle East.

The large pore sizes cause the water to relax close to its bulk value overlapping the gas signal, and resulting in a smeared peak at a long T2.

According to an embodiment of the present invention, these D-T2 maps are generated by model-independent inversion codes such as MEP. These model independent inversions do not require a priori input of the fluids diffusion or T2 values. According to one embodiment, the model independent inversions do not require any a priori knowledge of fluid properties nor what fluids are present. From these inversions, D-T2 maps or graphs are generated to display the resultant multi-dimensional NMR data across two, three or more axes in an easily readable form.

According to one embodiment, the D-T2 maps are used to improve the results of model-dependent inversion such as the MRF analysis. Specifically, MEP, and other model independent derived D-T2 maps provide an unbiased representation of the NMR data. As such, an overlay of the theoretical responses of the three most encountered fluids, i.e., water, oil, and gas indicates whether the responses need adjustments for use in model-based inversion.

For example, the MRF model (for oil, gas and water) states that the water and gas diffusion constants are independent of T2, and depend on temperature T and pressure P (for gas):

$$D_w(T2) = D_w(T) \quad (1)$$

$$D_g(T2) = D_g(T,P) \quad (2)$$

For oil, the diffusion constant is linearly proportional to T2, $$D_O(T2) = \lambda \times T2 \quad (3)$$

It follows from Equations (1)–(3) that two horizontal lines (i.e. at constant D values) representing the theoretical responses of water and gas, and a diagonal line representing the theoretical response of oil can be overlaid on a D-T2 map. Deviations from the ideal fluid responses will be evident in the maps as signals located away from the overlay lines. Once known, these deviations are applied to the model-based inversion. The result from the inversion provides an answer with improved accuracy based on the observations from the model-independent D-T2 maps.

Figure 8:
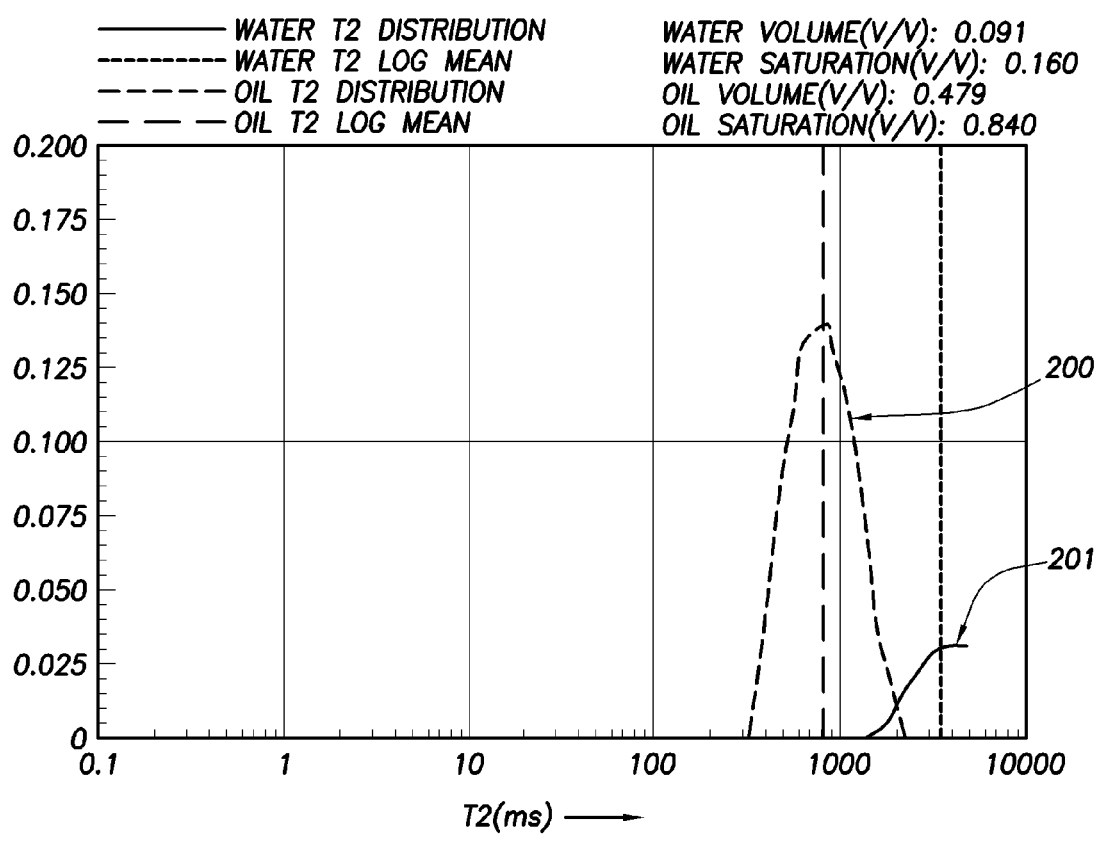
FIG. 8 is two dimensional graph according to a prior art inversion method.
Figure 9:
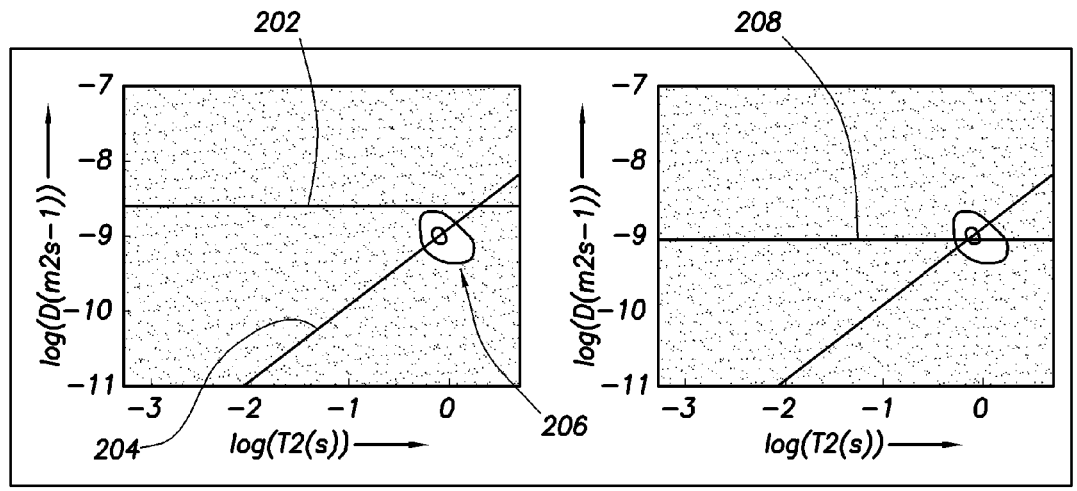
FIG. 9. is a NMR data map set showing correction of non-ideal effects according to one aspect of the disclosed subject matter.
Figure 10:
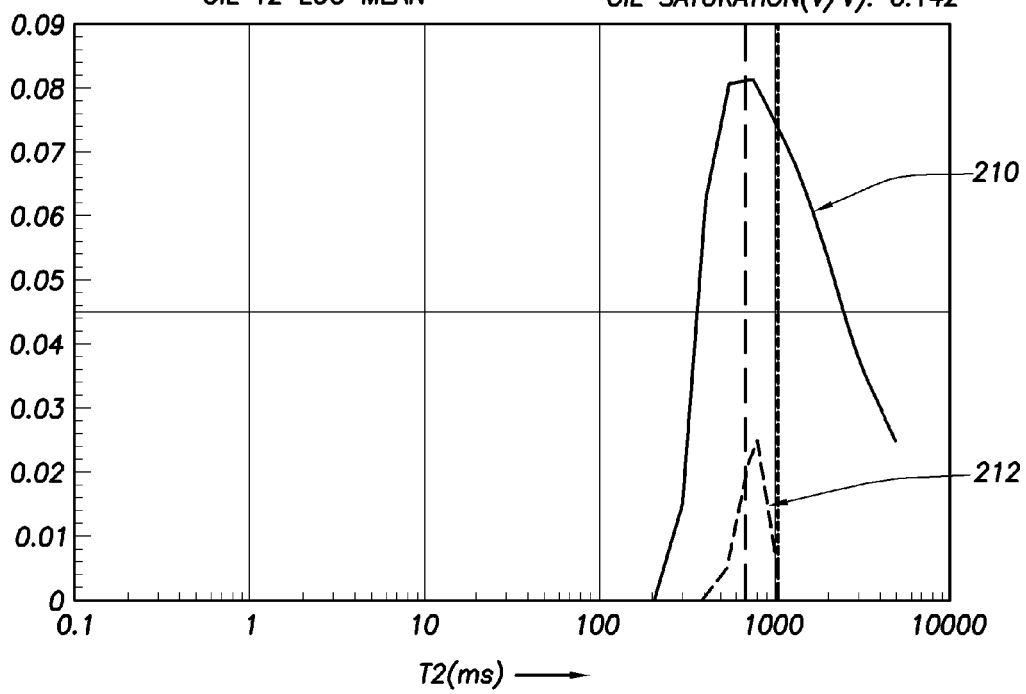
FIG. 10 illustrate a correction of a prior art inversion method according to the NMR data map set of FIG. 9.
Figure 11:
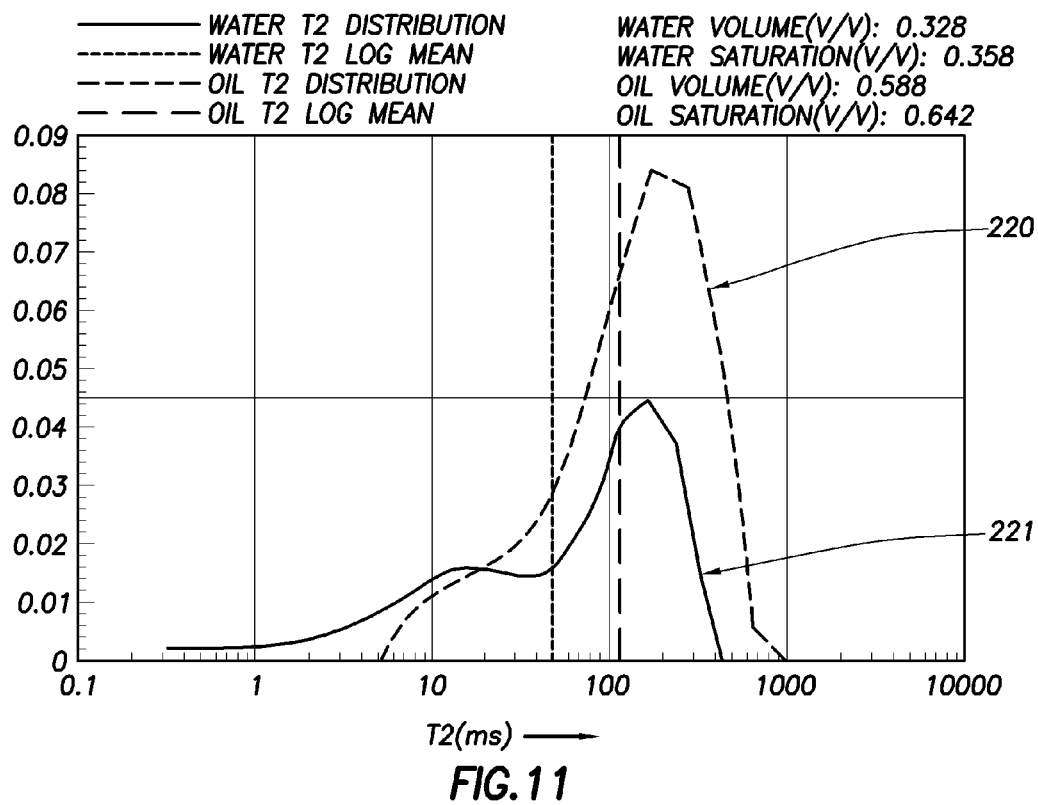
FIG. 11 is two dimensional graph according to a prior art inversion method.
Figure 12:
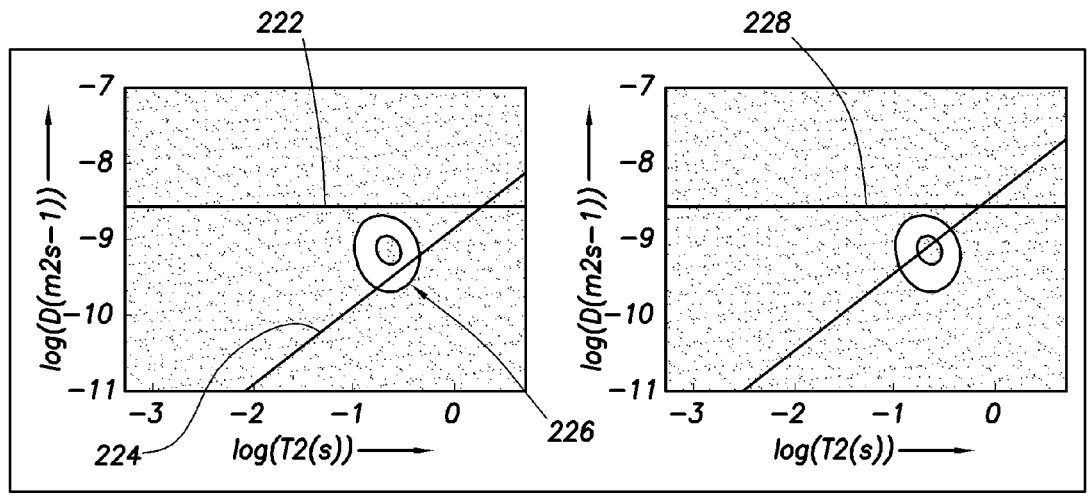
FIG. 12. is a NMR data map set showing correction of non-ideal effects according to one aspect of the disclosed subject matter.
Figure 13:
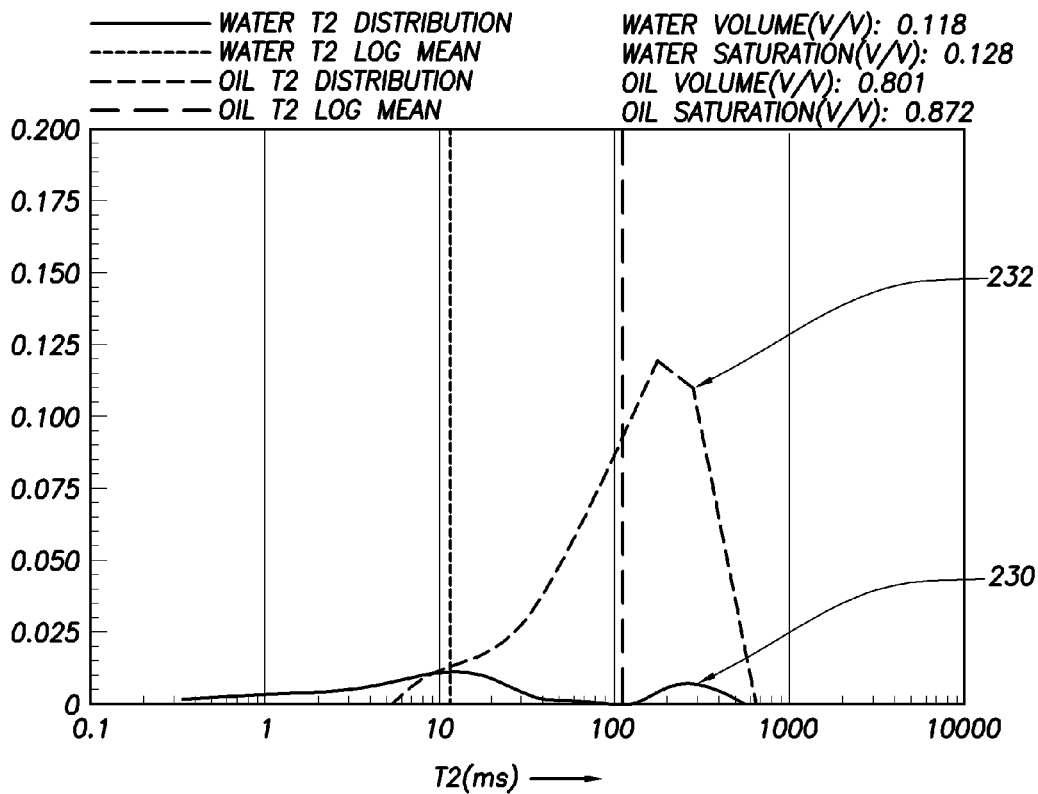
FIG. 13 illustrate a correction of a prior art inversion method according to the NMR data map set of FIG. 12.

FIGS. 8–10 illustrate the model-dependent inversion correction in a water based drilling fluid, cesium formate, and FIGS. 11–13 illustrate the correction in a primarily crude oil sample. FIG. 8 shows an exemplary model dependent based analysis, such as the MRF approach, for a cesium formate solution. FIG. 8 shows the model-based analysis having an oil peak 200 and a water peak 201. The model based analysis using the default water diffusion constant indicates mostly oil for cesium formate drilling fluid. FIG. 9 shows the D-T2 map on the left for the same data having the fluid instance or artifact 206 lying along the default oil diffusion line 204. Specifically, the D-T2 map on the left shows that the detected Cs formate fluid, the instance 206, has a much lower diffusion constant than pure water (the default), indicated by horizontal line 202. Thus it can be determined that the ideal water diffusion 202 is not correct for the Cs formate sample. Thus, in order to compute correct fluid saturations the effective "water" (Cs formate to be precise) diffusion constant must be reduced to 40% of its default value, represented by horizontal line 208. This corrected diffusion value is then programmed into the model based inversion. FIG. 10 shows the reprocessed MRF results obtained using a water diffusion constant reduced to 40% of its original value. The MRF results now correctly indicate predominantly water, shown at peak 210, having a very low oil signal, shown at peak 212. As such, the associated formation evaluation determinations such as water volume and saturation can be more accurately computed.

FIG. 11 shows a model dependent based analysis of a known crude oil sample. The results indicate the presence of oil, shown by peak 220, but also incorrectly indicates significant water saturation, indicated by peak 221. FIG. 12 shows the D-T2 map for the same data. On the left, the D-T2 map is shown with the default fluid overlay lines, the water diffusion represented by horizontal line 222 and the oil diffusion represented by line 224. The signal or instance 226 appears above the oil D-T2 correlation line 224 indicating that this oil has an unusually high diffusion to T2 ratio. Thus, it can be determined that the existing oil D-T2 line 224 is incorrect and requires adjustment. The same map is plotted on the right with a new oil D-T2 correlation line 228 that bisects the main signal peak. The MRF analysis is then run using an increased $$\lambda$$

value (see Eq (3)). The results of the reprocessed data are shown in FIG. 13. As expected, the MRF analysis now correctly predicts predominantly oil at peak 232, while indicating a very low water presence at curve 230.

In addition to assisting model-dependent interpretation techniques as shown above, complete quantitative petrophysical answers can be derived directly from the two-dimensional maps. Specifically, according to one application of the invention, quantitative measurements of porosity, permeability, fluid volumes, saturations, oil viscosity and other quantities can be derived from D-T2 maps. Compared to prior methods, additional interpretation is needed to derive more than previously utilized qualitative information. According to the disclosed subject matter, two approaches, a point-and-click approach and a diffusion log mean approach, are used to obtain quantitative answers.

According to one embodiment, a visual point-and-click approach is provided which allows a user to interact with a D-T2 map by focusing in on particular artifacts graphically shown on a map. The signal amplitude, A, from a suite of NMR pulse sequences can be expressed as $$A(WT, TE, t) = \sum_i \sum_j \sum_k f(i, j, k) H(WT, TE, t; i, j, k) + \delta(WT, TE, t) \quad (4)$$

where WT, TE, t are the wait time, echo spacing and time of the NMR pulse sequences, (i, j k) are the indices of the T2, D and T1/T2 distributions, f(i,j,k) is the amplitude of the three-dimensional component in the T2, D, T1/T2 space, H(WT, TE, t i, j, k) is the kernel of that component, and □ is a noise term.

Figure 14:
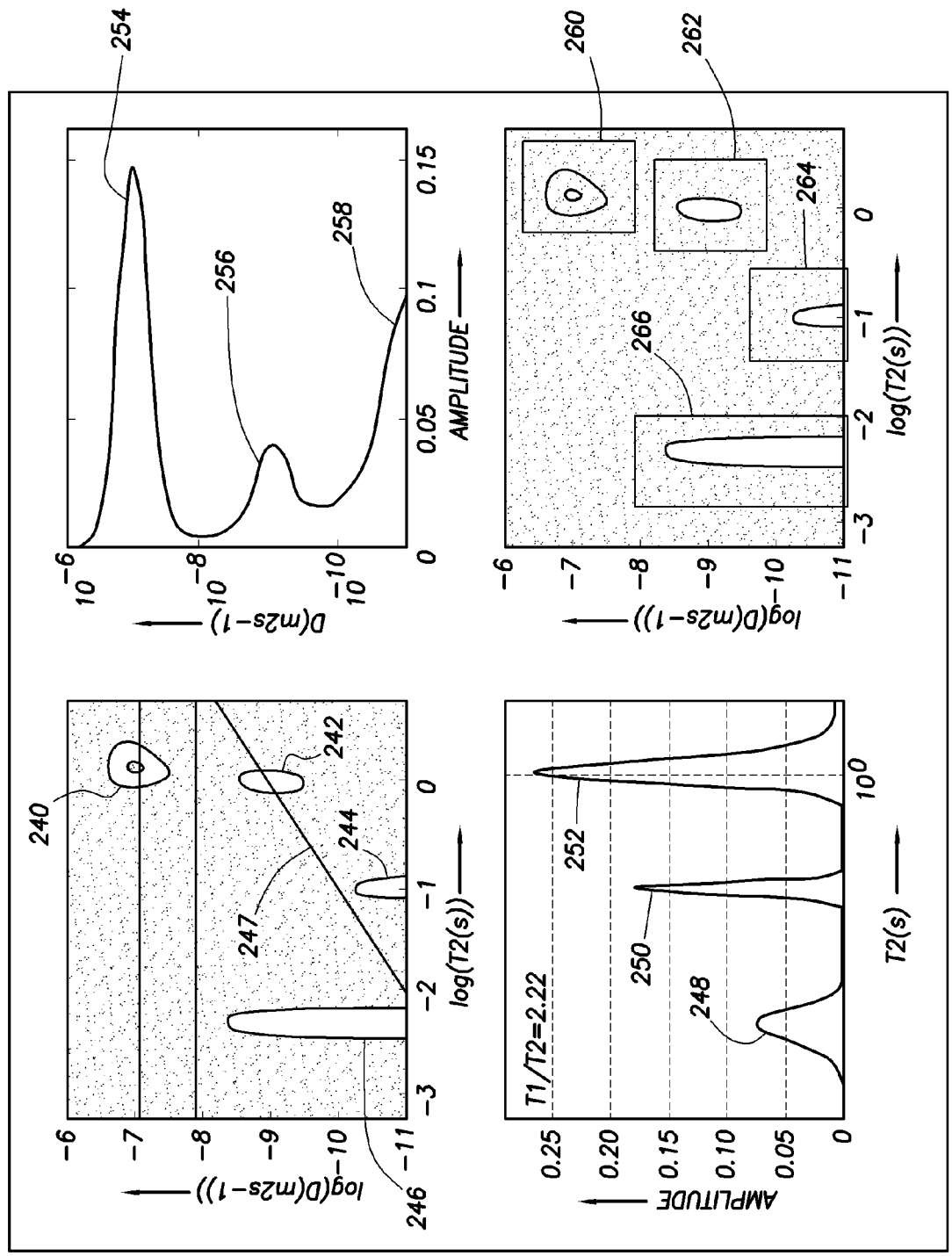
FIG. 14 is a set of NMR maps and graphs according to one formation evaluation method of the disclosed subject matter.

From the above equation (4), it can be seen that the D-T2 map is a representation of the signal amplitudes integrated across the k dimension (T1/T2) of the MEP inversion result. Therefore, in the favorable case where the fluids distributions in the D-T2 space are well separated as seen in FIG. 14, their respective volumes can be directly obtained by integrating the amplitudes in the D and T2 windows defined by each type of fluid. The respective saturations can then be derived by dividing the respective fluid volumes with the total fluid volume. The individual volumes must be corrected for hydrogen index, according to known methods, to give correct answers.

FIG. 14 illustrates an example according to one embodiment of the point-n-click approach having four fluids artifacts, 240, 242, 244 and 246, that are well separated in D-T2 space (top left pane). Note that the four fluids are not resolved in either T2 space (bottom left pane) or D space (top right pane). Specifically, the T2 and D space graphs indicate three instead of four fluids having separable properties. In the bottom left T2 graph, peak 248 corresponds to artifact 246 and peak 250 corresponds to artifact or fluid instance 244. However, peak 252 cannot resolve artifacts 240 and 242. In the top right diffusion distribution, peak 254 corresponds to artifact 240 and peak 256 corresponds to fluid instance 242. However, peak 258 cannot resolve artifacts 244 and 246.

According to prior methods, quantitative fluid answers could be obtained using T2 graphs. However, as shown, in some cases T2 maps cannot fully resolve multiple fluids having different diffusion properties. Known prior methods have gone a step further to use the D-T2 map to evaluate the accuracy (qualitatively) of the answers derived from the T2 graphs. According to an embodiment of the present invention, a visual point-n-click method uses the D-T2 map to determine quantitatively the respective volumes of each of the four fluids by integrating the signal amplitudes along T2 and D dimensions in the windows defined by the rectangles 260, 262, 264 and 266. Note that the use of other shapes to delineate the map region of interest, such as polygons or circles, may be employed in a similar manner. In this way, the disclosed methods advance the state of the art in part by resolving multiple fluids having similar T2 distributions and determining quantitatively certain formation evaluation answers once the fluid artifacts are separately identified.

According to one application of the point-and-click method, the interpreter can easily select the integration region of the D-T2 map using, for example, the computer mouse or a digitized pen. Selection of a region may also be performed automatically by a software algorithm, for example, based on a predetermined amplitude threshold. Note also that the interpretation of the fluid type is guided by overlaying the theoretical responses of gas, oil and water in the D-T2 map as seen in the top left pane. This step also may be performed automatically by a software application, for example, based on a proximity of a point of maximum amplitude to the theoretical gas, oil and water responses.

Figure 15:
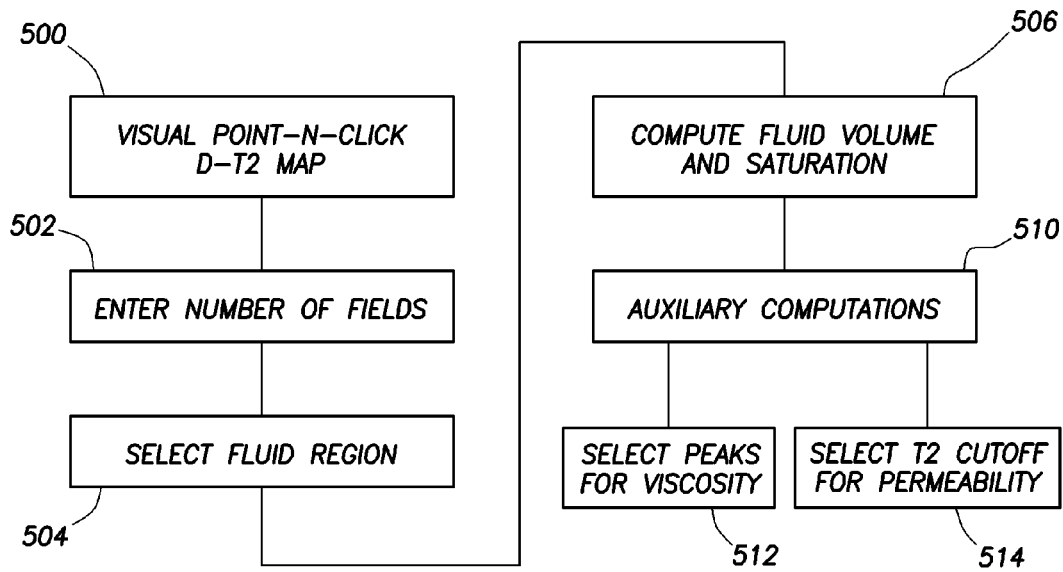
FIG. 15 is a flow diagram of the method illustrated in FIG. 14.

Turning to FIG. 15, illustrated is a flow diagram of the point-n-click approach. Beginning at step 500, the point-and-click routine begins with a D-T2 map. As mentioned, this D-T2 map is preferably generated using a model-independent inversion approach. Continuing at step 502, the user is asked to enter the type of fluid model to be used in the calculation. Typically, this will be done by inspection of the map. First, the user decides on the number of fluids. For example, if two amplitude clusters (bright spots) are present, then a two-fluid approach is chosen. Second, each fluid type is interpreted with the help of the overlay of theoretical responses of water, oil and gas. At step 504, the user selects the fluid region using a computer mouse. According to one embodiment, a box is displayed and manipulated to encompass substantially all the artifact on the D-T2 map. According to a embodiment, the final unselected region having a positive non-zero amplitude is accumulated and displayed to provide an indication to the user as to whether any substantial portions had been missed. According to another embodiment, a computer or software application selects an extent at least partially surrounding of each fluid instance based on a threshold amplitude.

Once the artifact has been selected, the fluid volume and saturation is calculated at step 506 by integrating over the selected region of the D-T2 map. Since the integration over the total map area gives total porosity, individual fluid saturations can be computed by dividing the fluid volumes with total porosity. It is appropriate to reiterate here that although the disclosed point-and-click method is discussed for exemplary purposes in the context of D-T2 maps, nearly any multi-dimensional map can be employed to determine a quantity of interest. Continuing at step 510, once fluid volume and saturation quantities, or other base values, have been determined, auxiliary computations at 510 can be requested by the user or automatically by the algorithm. For example, at step 512, viscosity can be determined by computing the mean T2 in the oil window, and using published oil viscosity-relaxation charts to estimate viscosity. Another example is to use the map-derived bound fluid volume to compute Timur-Coates permeability according to the equation k_Timur=a*phit^b*((phit bfv)/bfv)^c, where a, b, c are constants, phit is total porosity, and bfv is the bound fluid volume.

A second approach to directly determine quantitative results from D-T2 maps involves a determination of log-mean diffusion ($D_{LM}$). In standard MRF analysis, the raw data is fit directly using the constraints of Eqs. 1, 2 and 3. Similar constraints are imposed for other prior art model dependent inversions. An alternative approach, as disclosed herein is to use the maps themselves as input to derive the solution which MRF attempts. Since the information contained in the maps is essentially identical to that of the original data, the two methods of solution should be comparable. In practice, however, the data is often lacking in diffusion information and therefore, the different fluids D-T2 amplitudes are spread over large areas of the map (resolution). This is in contrast to the ideal situation for application of the point-and-click method where each fluid artifact is substantially separated from other fluid instances. The problem then consists of reassigning the amplitude spread in the diffusion axis to the different formation fluids. According to this second approach, an approximate way to do this is to use the geometric mean diffusion rate for each T2, notated $D_{LM}(T2)$, computed from the maps, and redistribute the amplitude at this T2 according to the chosen fluid model. For example, for a model consisting of water and oil it is convenient to define an apparent water saturation at each T2 value, SXO(T2), $$D_{LM}(T2)=D_W(T2)^{SXO(T2)}D_O(T2)^{1-SXO(T2)} \qquad (5)$$

$$SXO(T2) = \frac{\ln(D_{LM}(T2)/D_O(T2))}{\ln(D_W(T2)/D_O(T2))} \qquad (6)$$

Separate water and oil T2 distributions, $F_{H2O}$, and $F_{OIL}$, can now be derived, $$F_{H2O}(T2_i)=SXO(T2_i) \times F(T2_i) \qquad (7)$$

$$F_{OIL}(T2_i)=(1-SXO(T2_i)) \times F(T2_i) \qquad (8)$$

$$F(T2_i) = \sum_j \sum_k F(T2_i, D_j, Tl_k/T2_k) \qquad (9)$$

The $D_{LM}$ approach is most effective when the fluid model has only 2 components. In such a case, a best guess of the fluid model is provided to the software algorithm. In the case of a model involving more than 2 components, the extra components are successively eliminated from the D-T2 map. For example, for a water-oil-gas model, the gas component can be eliminated from the map using the Visual-Point-and-Click approach as described above and the D-T2 map re-normalized for the water-oil model. In practice, because the formation always contains irreducible (bound) water, the final reduced model is either water-oil or water-gas.

Figure 16:
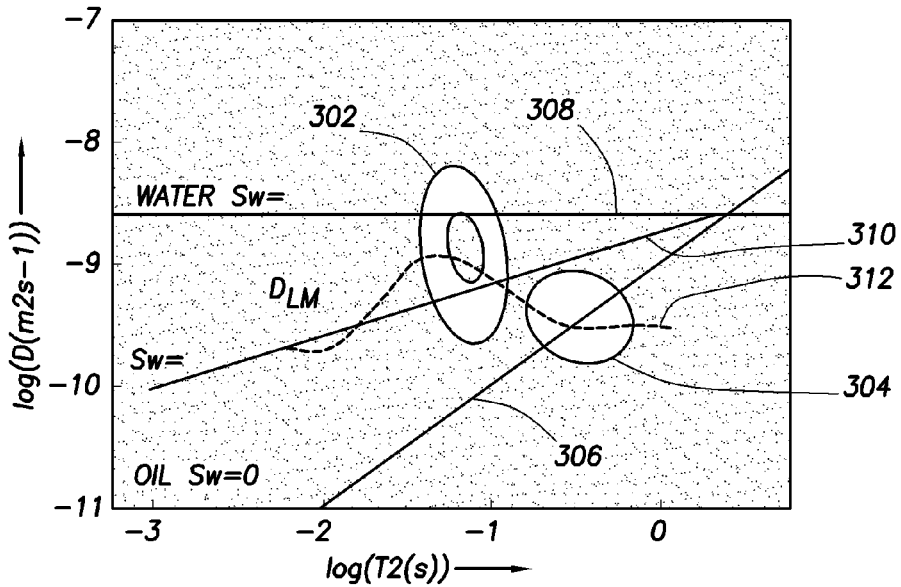
FIG. 16 is a multi-dimensional map or graph of another formation evaluation method of the disclosed subject matter.

FIG. 16 illustrates a graphical representation of an exemplary $D_{LM}$ approach. Here, the D-T2 map shows two different fluid instances. The fluid instance or artifact 304 is likely oil due to its proximity on the theoretical oil response overlay 306. According to one embodiment, quantitative evaluation of fluid instance 304 can be determined directly from the D-T2 using the above described point-and-click method. In this case, after artifact 304 has been evaluated, it can be deleted and the map renormalized containing only the fluid instance 302. However, since artifact 304 is not well separated from artifact 302, the results of the point-and-click depend greatly on the delineation process. In another embodiment, the $D_{LM}$ approach may include both fluid instances 302 and 304. Turning attention to fluid instance 302, the analysis is not as clear. Specifically, the distribution associated with fluid instance 302 lies between what one would expect for either water or oil, indicated by the water overlay 308 and the oil overlay 306. Further, because the fluid type cannot be determined, any integration over the distribution would not provide accurate formation evaluation answers. A solution, according to one embodiment, is to compute the mean diffusion $D_{LM}$ 312 across the distribution 302. Each value of $D_{LM}$ is then used to re-assign the signal amplitude according to the separate fluid diffusion rates as indicated by Eq. 6. The re-assignment is linear in log space and based on the proximity with respect to the fluids diffusions responses. For example, if $\log(D_{wat})$=a, $\log(D_{oil})$=b, and DLM=c, then the water saturation is $S_w$=(c b)/(a b).

Figure 17:
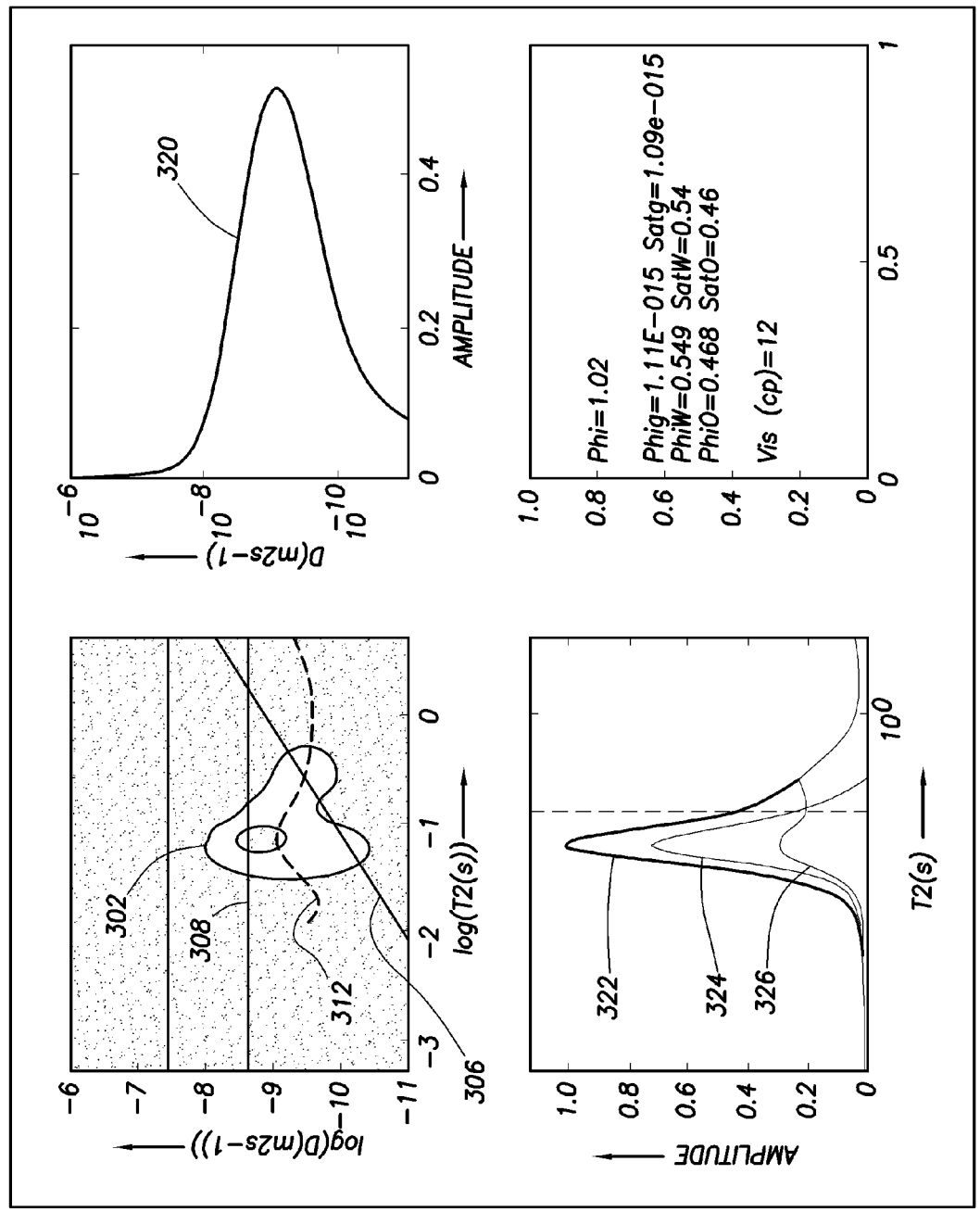
FIG. 17 is a set of NMR maps and graphs according to the method illustrated in FIG. 16.

FIG. 17 provides another example using the $D_{LM}$ approach derived for a D-T2 map distribution. Here again, the prior art T2 graph cannot resolve the fluid type of instance 302. Specifically, according to prior methods, the T2 graph at the bottom-left panel shows only the total curve 322 (curves 324 and 326 are computed using the methods disclosed herein). Furthermore, the diffusion distribution graph in the upper-right panel similarly cannot resolve more than one fluid type as indicated by diffusion curve 320. According to the disclosed $D_{LM}$ approach, the $D_{LM}$ is multiplied by the overall T2 distribution as per Eqs 7 and 8 to yield the water distribution 324 and oil distribution 326 seen in the bottom left panel. Integrations of the water and oil distributions then give the water volume (PhiW) and the oil volume (PhiO) seen in the bottom right pane. The oil log mean T2 can also be computed from the oil distribution (vertical dash line) from which the oil viscosity is estimated (Vis).

Figure 18:
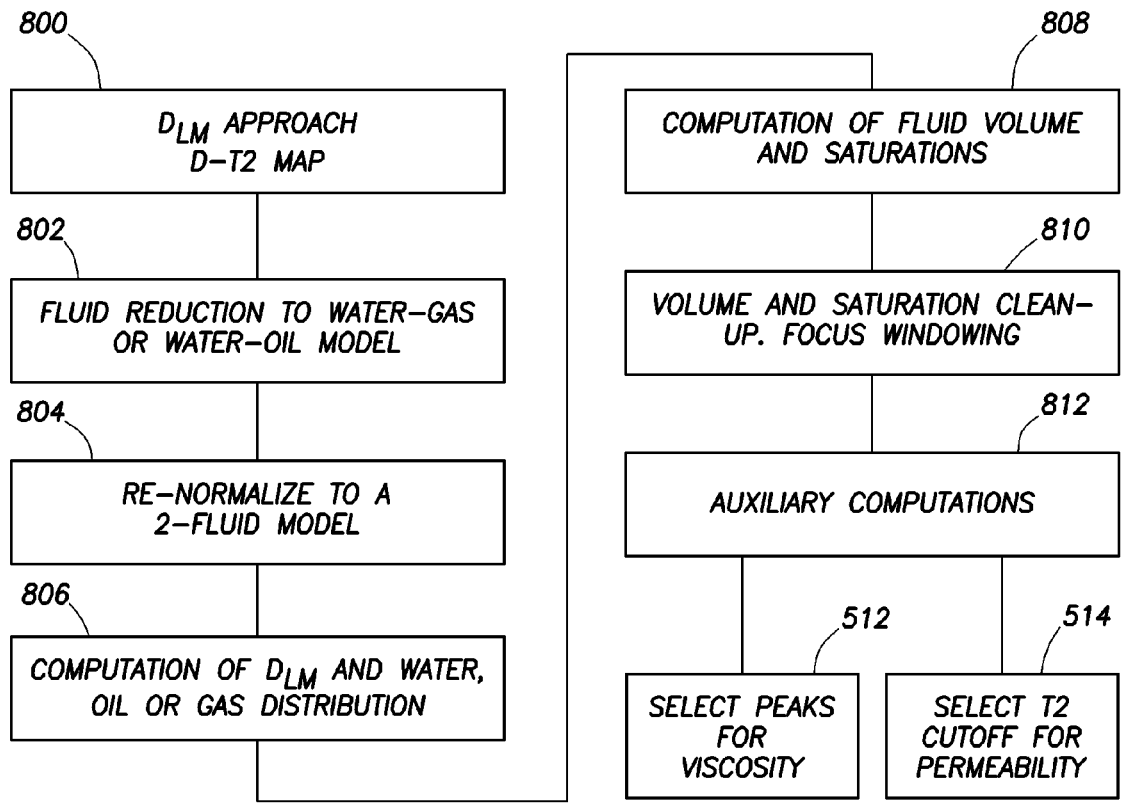
FIG. 18 is a flow diagram of the method illustrated in FIGS. 16 and 17.

FIG. 18 shows a flow chart of an exemplary method employing a $D_{LM}$ determination. Beginning at step 800, a D-T2 map is generated or imported from a model independent inversion process. At step 802, a fluid model is selected by the user based in part on a visual inspection of the D-T2 map or prior knowledge of the sample, or a combination of both. The most common fluid models include water-oil or water-gas, although other combinations are equally applicable. Additionally at step 802, any fluid artifacts not included in the selected fluid model, but present on the D-T2 map, are removed from the distribution. This may either be performed manually using a computer mouse, for example, or automatically by software based on the proximity of an unwanted artifact to the theoretical response of the fluid that is not part of the model. For example, for a selected water-oil model, software can detect that a concentration of amplitude, indicating the likely presence of a fluid, occurs near the theoretical gas response. An edge-detection routine is executed to determine the extent of the artifact, interpreted as a gas, and then delete that region of the map from the total distribution.

Once the unwanted artifacts have been removed, the D-T2 map at step 804 is normalized to the selected two-fluid model. At step 806, the log mean diffusion is calculated over the extent of the amplitude concentration. According to one embodiment, the $D_{LM}$ curve is displayed as an overlay on the D-T2 map. From there, and as described above, the fluid volume and saturation is determined at step 808 using Eq. 6 and 7. Continuing at step 810, the volume and fluid saturation indications are adjusted by focus windowing to improve the accuracy of the evaluation answers. Specifically, window focusing is performed to impose a saturation value, over a T2 region, in effect overriding the saturation computed by DLM. This is preferred to counteract the unwanted effects of restricted diffusion, internal gradients etc. mentioned before. Finally, at step 812, once fluid volume and saturation quantities, or other base values, have been determined, auxiliary computations at 510 can be requested by the user or automatically by the algorithm. For example, at step 512, viscosity can be determined by computing the mean T2 of the oil distribution and using published oil viscosity-relaxation charts to estimate viscosity.

It should be noted that the above described exemplary approaches, including the point-and-click method and the $D_{LM}$ method may be employed on variations of the D-T2 maps. For example, it can be helpful to define a D-T2 map for a certain T1/T2 ratio. In the context of the point-and-click method, the D-T2 inversion results are normally integrated over the third dimension which is T1/T2 ratio. However, it is also possible to decompose the total signal into separate results corresponding to each T1/T2 value and benefit from T1 information in the fluid interpretation. Essentially, this means that a D-T2 map is generated for each T1/T2 plane.

Figure 19:
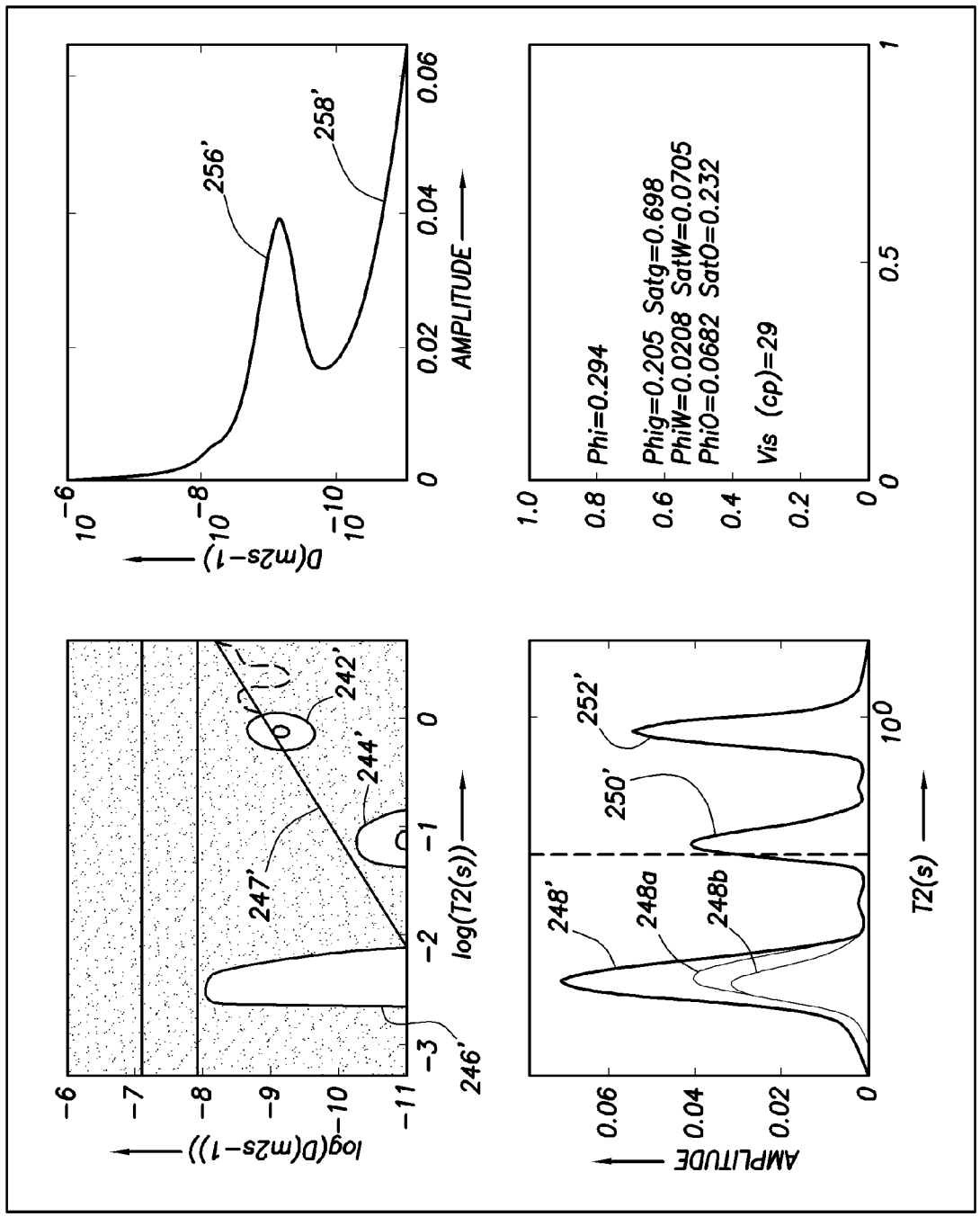
FIG. 19 is another set of NMR maps and graphs of a formation evaluation method of the disclosed subject matter.

FIG. 19 provides an example where elimination of one fluid phase is necessary so that the $D_{LM}$ approach can be applied. The D-T2 map in the top left panel is derived from the D-T2 map shown in FIG. 14. The gas peak 240 has been eliminated from the original map of FIG. 14 using the visual point-and-click approach and the remaining amplitude is subsequently re-normalized to give the new map shown in FIG. 19. Specifically, the re-normalized map shows artifacts 242" and 244", both believed to be oils, and artifact 246", believed to be water but unclear. Note the absence of the gas diffusion amplitude 254 in the top right pane. Here again, neither diffusion peak 256" and 258" fully resolve any of the artifacts. Specifically, each diffusion peak contains information from multiple artifacts, peak 258" containing information from fluid instances 244" and 246", and to a lesser degree, peak 256" containing information from fluid instances 242" and 246". Initial fluid volumes and saturations are displayed in the bottom right pane. However, from the D-T2 map and the T2 graph showing an estimated oil peak 248a and an estimated water peak 248b, it is apparent further interpretation is needed to better determine the fluid type associated with artifact 246".

Figure 20:
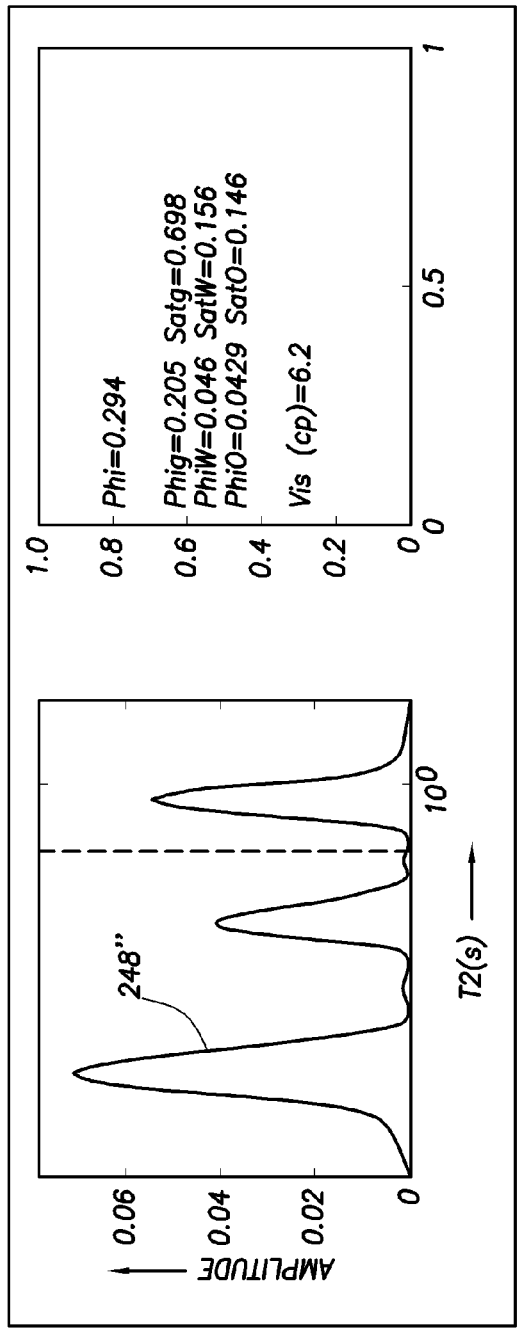
FIG. 20 is a set of corrected NMR graphs according to the method illustrated in FIG. 19.

In FIG. 20, the peak appearing at short T2 (~5 ms), peak 248" in FIGS. 14 and 19 is believed to be water. The breadth of the peak in the D-T2 map reflects the uncertainty in the corresponding diffusion rate. This is due to lack of information in the original NMR data. With a priori knowledge we can manually assign this peak as water using the window focusing method, resulting in peak 248''''. Having done this, the water volume, oil volume and the T2 log mean of oil have changed compared to their initial values shown in FIG. 19.

Figure 21:
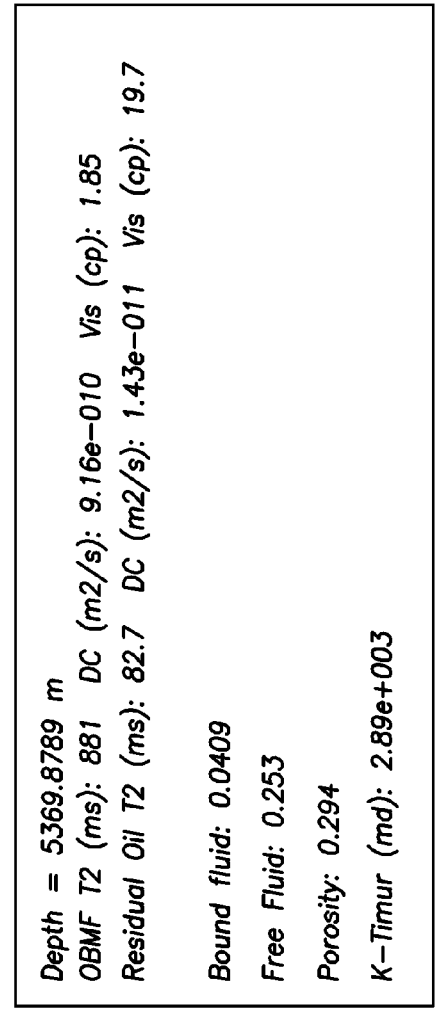
FIG. 21 is a screen shot illustrating exemplary formation evaluation answers provided by the disclosed subject matter.

FIG. 21 shows an example of interactive computation of the two oil viscosities that correspond the two bright spots along the oil response line 247 and 247'' on D-T2 map (FIGS. 14 and 19). Timur-Coates permeability is also computed interactively for a user-defined T2 cutoff.

While the invention has been described with respect to a limited number of embodiments, those skilled in the art, having the benefit of this disclosure, will appreciate that other embodiments can be devised which do not depart from the scope of the invention as disclosed herein. For example, embodiments of the invention may be practiced with a wireline tool as well as a LWD or MWD tool. In addition, embodiments of the invention may be practiced on a fluid sample removed by a formation tester and the NMR measurements are either acquired in the formation tester or in a laboratory. Further, the disclosed methods are not acquisition specific and may be applied to nearly all datasets regardless of whether a CPMG, diffusion editing or other pulse sequence is used. Accordingly, the scope of the invention should be limited only by the attached claims.

The invention claimed is:

1. A method for formation evaluation results from a multi-dimensional representation of nuclear magnetic resonance data, the method comprising the steps of:
   obtaining a set of NMR data for a fluid sample;
   computing from the set of NMR data a multi-dimensional distribution using a mathematical inversion based on a maximum entropy process independent of prior knowledge of fluid sample properties;
   displaying the multi-dimensional distribution as an at least two-axis graph;
   identifying at least one fluid instance on the graph representing a probable existence of a detected fluid; and
   computing a quantitative formation evaluation value for the at least one fluid instance based on the multi-dimensional distribution associated with the at least one fluid instance.

2. The method of claim 1, wherein the multi-dimensional distribution is displayed along a fluid diffusion axis and a T2 relaxation axis.

3. The method of claim 1, wherein the graph includes an overlay with ideal diffusion and T2 relaxation values.

* * * * *